US008506910B2

(12) United States Patent
Singh et al.

(10) Patent No.: US 8,506,910 B2
(45) Date of Patent: Aug. 13, 2013

(54) PROCESS AND SYSTEM FOR PRODUCING LIQUID FUEL FROM CARBON DIOXIDE AND WATER

(75) Inventors: Shwetank Singh, Reykjavik (IS); Omar Freyr Sigurbjornsson, Reykjavik (IS); Kim-Chinh Tran, Gardabaer (IS)

(73) Assignee: CRI EHF, Gardabaer (IS)

( * ) Notice: Subject to any disclaimer, the term of this patent is extended or adjusted under 35 U.S.C. 154(b) by 0 days.

(21) Appl. No.: 13/452,073

(22) Filed: Apr. 20, 2012

(65) Prior Publication Data
US 2012/0201717 A1  Aug. 9, 2012

Related U.S. Application Data

(62) Division of application No. 11/725,716, filed on Mar. 20, 2007, now Pat. No. 8,198,338.

(60) Provisional application No. 60/783,405, filed on Mar. 20, 2006.

(30) Foreign Application Priority Data

Mar. 20, 2006  (IS) .............................................. 8367

(51) Int. Cl.
*B01J 8/04* (2006.01)
*B01J 8/00* (2006.01)
*B01J 19/00* (2006.01)
*C07C 27/00* (2006.01)
*C07C 27/06* (2006.01)

(52) U.S. Cl.
USPC ........... 422/630; 422/129; 422/187; 422/600; 518/700; 518/701; 518/702; 518/703; 518/704; 518/706; 518/707; 518/708; 518/711; 518/713; 518/714; 518/715; 518/716; 518/717; 518/718; 518/719; 518/720; 518/721

(58) Field of Classification Search
USPC ......... 422/129, 162, 187, 600, 630; 423/414; 518/700–704, 706–708, 711–721
See application file for complete search history.

(56) References Cited

U.S. PATENT DOCUMENTS 4,059,076 A * 11/1977 Kosaka et al. .................... 123/3
4,087,259 A    5/1978 Fujitani et al.
(Continued)

FOREIGN PATENT DOCUMENTS
DE       19522083       10/1996
DE       20320020        5/2004
(Continued)

OTHER PUBLICATIONS

Machine translation of DE 19522083 A1, which was submitted in the IDS and published on Oct. 2, 1996.*

(Continued)

*Primary Examiner* — Walter D Griffin
*Assistant Examiner* — Natasha Young
(74) *Attorney, Agent, or Firm* — Jonathan C. Parks, Esq.; Pietragallo Gordon Alfano Bosick & Raspanti, LLP (57) ABSTRACT

A process and system for producing high octane fuel from carbon dioxide and water is disclosed. The feedstock for the production line is industrial carbon dioxide and water, which may be of lower quality. The end product can be high octane gasoline, high cetane diesel or other liquid hydrocarbon mixtures suitable for driving conventional combustion engines or hydrocarbons suitable for further industrial processing or commercial use. Products, such as dimethyl ether or methanol may also be withdrawn from the production line. The process is nearly emission free and reprocesses all hydrocarbons not suitable for liquid fuel to form high octane products. The heat generated by exothermic reactions in the process is fully utilized as is the heat produced in the reprocessing of hydrocarbons not suitable for liquid fuel.

10 Claims, 7 Drawing Sheets

(56) References Cited

U.S. PATENT DOCUMENTS

| | | | |
|---|---|---|---|
| 4,418,236 A | 11/1983 | Cornelius et al. | |
| 4,788,369 A | 11/1988 | Marsh et al. | |
| 4,844,837 A | 7/1989 | Heck et al. | |
| 4,910,227 A | 3/1990 | Brown et al. | |
| 5,342,702 A | 8/1994 | MacGregor | |
| 5,500,449 A | 3/1996 | Benham et al. | |
| 5,602,289 A * | 2/1997 | van Dijk | 585/315 |
| 5,648,582 A | 7/1997 | Schmidt et al. | |
| 6,254,807 B1 | 7/2001 | Schmidt et al. | |
| 6,265,453 B1 | 7/2001 | Kennedy | |
| 6,306,917 B1 | 10/2001 | Bohn et al. | |
| 2002/0120017 A1 | 8/2002 | Bohn et al. | |
| 2006/0211777 A1* | 9/2006 | Severinsky | 518/702 |
| 2007/0244208 A1 | 10/2007 | Shulenberger et al. | |

FOREIGN PATENT DOCUMENTS

| | | | |
|---|---|---|---|
| JP | 57126434 | | 8/1982 |
| JP | 03200734 | | 9/1991 |
| JP | 03200734 A | * | 9/1991 |
| WO | 03/035591 | | 5/2003 |
| WO | 2006/099573 | | 9/2006 |

OTHER PUBLICATIONS

Inui et al., Effective Conversion of Carbon Dioxide to Gasoline, 1992, Energy Convers. Mgmt, vol. 33, No. 5-8, pp. 513-520.*

English translation of JP 03-200734 A, which was published Sep. 2, 1991.*

Schliesinger, M.D. et al., Fisher-Tropsch Synthesis in Slurry Phase, Engineering and Process Development, vol. 43 (6): 1474-1479 (1951).

* cited by examiner

PROCESS AND SYSTEM FOR PRODUCING LIQUID FUEL FROM CARBON DIOXIDE AND WATER

CROSS-REFERENCE TO RELATED APPLICATION

This application is a divisional of U.S. patent application Ser. No. 11/725,716 filed Mar. 20, 2007, which claims priority to U.S. Provisional Application Ser. No. 60/783,405 filed Mar. 20, 2006 and Iceland Patent Application No. 8367 filed Mar. 20, 2006.

FIELD OF INVENTION

The present invention is broadly within the field of energy conversion and relates to processes and systems for producing hydrogen by electrolysis of water, processes for reacting hydrogen with carbon dioxide for producing methanol and/or producing syngas and processes for synthetic liquid fuel production.

BACKGROUND OF THE INVENTION

There are four global issues of concern that are addressed by the current invention;
  i) The diminishing capacity of the world production of mineral oil;
  ii) The effect of the increasing carbon dioxide emission on global warming;
  iii) The contribution from combustion of sulfur-containing fuel to acidification of rainwater;
  iv) The effective and economic utilization of available renewable energy sources may not be suitable for conventional applications.

Current evaluation of the world oil production predicts the production to peak around the year 2010. As the world production capacity is believed to behave like a bell curve the expectations are that we will have diminishing production capacity within a few decades from now. Demand on the other hand rises rapidly and it has become foreseeable that in fairly short time, gasoline production will not meet demand.

It is therefore very important to develop processes that allow utilization of alternative energy sources to provide fuel that can immediately substitute the currently used gasoline and diesel distilled from petroleum oil. Such fuel which is compatible with combustion engines as they are today will render the need for major, time consuming, technical developments and infrastructural changes unnecessary.

Currently, two processes have been used on industrial scale to produce synthetic liquid hydrocarbon fuel. One is the SASOL process which is based on classic Fisher-Tropsch chemistry and converts coal to syngas, which is converted to a variety of hydrocarbons via the Fisher-Tropsch synthesis. The other is the Mobil Methanol-to-Gasoline process (MTG), which was utilized on large scale in New Zealand to convert natural gas to high octane gasoline fuel.

Syngas or synthesis gas is a term used for gases of varying composition that are generated in coal gasification, steam reforming of natural gas and some types of waste-to-energy facilities. The name comes from their use in creating synthetic petroleum for use as a fuel or lubricant via Fischer-Tropsch synthesis. Syngas consists primarily of carbon monoxide and hydrogen, and can be produced from natural gas through steam reforming: $CH_4+H_2O \rightarrow CO+3H_2$, partial oxidation: $CH_4+\frac{1}{2}O_2 \rightarrow CO+2H_2$, or combination of both.

The Fisher Tropsch process was developed by the German researchers Franz Fisher and Hans Tropsch in the 1920s. It is a well documented process that has been used on industrial scale for production of diesel and other synthetic petroleum products for decades. This process is used by a number of companies today to produce low-sulfur diesel and other petroleum products on large scale. For example, SASOL has implemented this process since 1955 to produce petroleum fuel, AMSOIL introduced their first synthetic diesel in 1975 and since 1993 Shell operates a 14700 bbl/day GTL plant in Malaysia.

The conversion of syngas, obtained from natural gas, to methanol is a very well documented process. The process has been run on industrial scale for decades and the world production of methanol from natural gas is now around 30 MMtpa (million metric tons per annum).

The conversion of methanol to gasoline using the Mobile methanol to gasoline process (MTG) is a viable alternative to the Fisher-Tropsch synthesis when converting syngas to liquid fuel. This process, where the syngas is first converted to methanol and the methanol is converted in a second step, over dimethyl ether (DME) to high octane gasoline, went first on stream in New Zealand in 1985 and was producing about 14,500 B/D a year later. Since 1997 the New Zealand facilities are used exclusively for methanol production.

The global carbon dioxide emission has grown enormously in the past 50 years. In 1950 the global emission was about 1000 million tons carbon equivalent, but has now reached close to 10,000 million tons carbon equivalent. About one fourth of this is industrial emission. As a consequence thereof, the concentration of carbon dioxide in the atmosphere is generally estimated to have increased about 30% from pre-industrial times. Due to the greenhouse effect of carbon dioxide, this enormous emission and increased levels cause increasing concern about the consequences of global warming.

It is therefore an important challenge to develop a process that allows recycling carbon dioxide to a valuable product such as liquid fuel. It is even more beneficial to develop a process to recycle carbon dioxide to a liquid fuel that is equivalent or even superior to the currently used gasoline and diesel, and can substitute these without any need for technical or infrastructural changes.

To date, commercially viable solutions have not been provided for producing liquid fuels from carbon dioxide and water. The present invention seeks to address this problem by a novel combination of several processes for conversion of electrical energy to chemical energy in the form of synthetic liquid hydrocarbon fuels that can readily replace conventional liquid fuels from natural oil reserves.

SUMMARY OF THE INVENTION

The present invention provides an integrated, nearly emission-free process for conversion of carbon dioxide and water to liquid fuel, such as high octane gasoline or diesel, suitable to drive combustion engines. The process may also be used to produce other hydrocarbons or hydrocarbon mixtures suitable for driving conventional combustion engines or hydrocarbons suitable for further industrial processing or other commercial use. Intermediate products such as methanol or dimethylether may also be generated by the production process of the invention. The overall process comprises in a preferred embodiment the conversion of water and carbon dioxide to C5+hydrocarbons (i.e., with five or more carbon atoms), preferably C5-C10 hydrocarbons. The overall process may also encompass the conversion of water and carbon dioxide to high cetane diesel or other liquid hydrocarbon mixtures suitable for driving conventional diesel combustion engines.

Accordingly, the present invention provides in one aspect a process for production of liquid fuel from carbon dioxide and water using electricity comprising: providing water and electricity and electrolyzing the water into hydrogen and oxygen, providing carbon dioxide and reacting it with the obtained hydrogen to produce methanol and/or carbon monoxide and water, where said methanol can comprise the desired final product or be reacted further to liquid hydrocarbon fuel, or, in the case of carbon monoxide intermediate production, reacting the obtained carbon monoxide with hydrogen in one or more steps to produce liquid fuel, which can be methanol or other liquid fuel such as liquid hydrocarbon fuel.

Thus, in one embodiment, the process comprises: providing water and electricity and electrolyzing the water into hydrogen and oxygen; providing carbon dioxide and reacting it with the obtained hydrogen to produce carbon monoxide and water; and reacting the obtained carbon monoxide and hydrogen in one or more steps to produce methanol or liquid hydrocarbon fuel without intermediate methanol production, where said methanol can optionally be processed further to liquid hydrocarbon fuel.

Said carbon monoxide may be mixed with carbon dioxide for the further reactions to obtain liquid fuels.

Another aspect of the invention provides a process for production of liquid fuel from carbon dioxide and water using electricity, comprising: providing water and electricity and electrolyzing the water into hydrogen and oxygen, and providing carbon dioxide and reacting with the obtained hydrogen to produce in a one step process liquid fuel.

DETAILED DESCRIPTION

Electrolysis of water to produce hydrogen and oxygen has been applied for a number of years on industrial scale and electrolytic hydrogen production systems are commercially available from a number of sources. Where water and electricity are available hydrogen production may, therefore, easily be installed. Hydrogen has been suggested as a future energy carrier replacing gasoline and diesel for fueling vehicles and ships, at least in locations where renewable energy is abundant in order to produce hydrogen by electrolysis or, as is more commonly used today, by steam reforming of natural gas (as a component of syngas, as mentioned above).

Electricity is an energy form that may be produced from alternative and renewable energy sources such as geothermal sources, solar power, wind energy, hydro-power, and ocean thermal- or kinematic-power. It is also produced in large quantities from nuclear power and may be produced through combustion of waste products (which would simultaneously produce $CO_2$). Electricity may also be made available through efficient utilization of off-peak power.

Carbon dioxide is generated in vast quantities in industrial processes such as aluminum smelting, ammonia production, cement production, iron smelting, ferro-alloy production, steel production, lime production, glass production and more, and also in large quantities from combustion processes such as in coal or gas power plants, vehicle operation and incineration or waste disposal. Carbon dioxide is also released in considerable quantities from geothermal power plants. Carbon dioxide is therefore available in close to unlimited quantities. Current technologies to capture carbon dioxide from gas streams on a large scale are mainly based on absorption on to amine based solvents. Such systems, like the CANSOLV®CO2 Capture System (Cansolv Technologies Inc., Montreal, Canada) are commercially available and are operated in a variety of industrial processes. Other methods, based on physical or chemical solvents, membranes, solid sorbents, or cryogenic separation, have also been used to capture $CO_2$. What specific capture technology is the most suitable depends on the process conditions under which it must operate. For the present invention, the skilled person can readily adopt any of the mentioned known techniques, depending on the specific source of $CO_2$ that is being utilized in each specific plant.

Depending on reaction conditions and catalyst selectivity, methanol can either be produced directly from $CO_2$ and $H_2$ or via CO which is formed in the competing reverse water gas shift reaction. The reverse water gas shift reaction has been shown to be a feasible method to convert carbon dioxide to carbon monoxide with close to 100% equilibrium conversion. This opens up the possibility to produce high quality syngas of any desirable composition from hydrogen and carbon dioxide.

From methanol, high octane gasoline may be produced over the dimethyl ether as intermediate. Likewise, high octane gasoline may also be produced from syngas via the intermediates methanol and dimethyl ether. High cetane diesel and other hydrocarbons may also be produced directly from syngas using the Fisher-Tropsch process or from methanol as the primary feed.

Accordingly, it is highly advantageous to combine these processes in an efficient way to produce sulfur-free, high octane gasoline or high cetane diesel which can immediately replace the currently used gasoline and diesel distilled from petroleum oil without time-consuming technical developments and major infrastructural changes.

Figure 1:
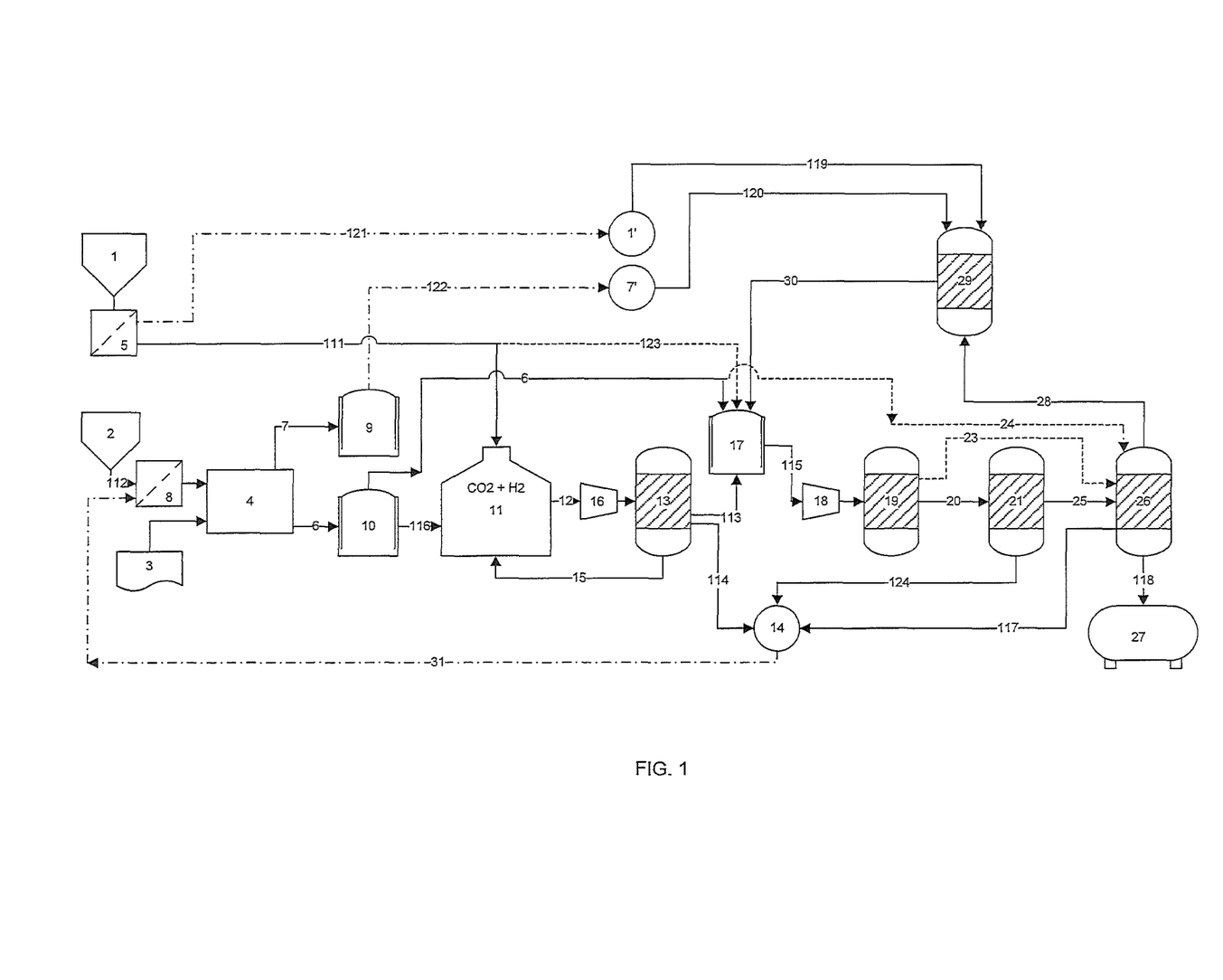
FIG. 1 shows a schematic overview of a system showing interactions of different sub units and also the process lines showing the connections between sub units according to the invention: an electrolysis unit 4, a RWGS reactor 13, a methanol reactor 19, DME reactor 21 and gasoline reactor 26.

FIG. 1 shows a flow diagram for the overall process. Individual steps in the process and variations thereof are detailed in the description of preferred embodiments. The overall chemistry and the energy balance of the process is shown in Formulas 1 through 8. The heat of reactions for formulas 1 through 7 is calculated from the corresponding heats of formation. For a (—$CH_2$—) unit the heat of formation is calculated as ⅛th of the heat of formation of octane.

| | | | |
|---|---|---|---|
| 1. | $6H_2O\ (l) \rightarrow 6H_2\ (g) + 3O_2\ (g)$ | 1,710 kJ | Electrical energy |
| 2. | $2CO_2\ (g) + 2H_2\ (g) \rightarrow 2CO\ (g) + 2H_2O\ (g)$ | 86.2 kJ | Heat |
| 3. | $2CO\ (g) + 4H_2\ (g) \rightarrow 2CH_3OH\ (g)$ | −181.6 kJ | Heat |
| 4. | $2CH_3OH\ (g) \rightarrow CH_3OCH_3\ (g) + H_2O\ (g)$ | −24 kJ | Heat |
| 5. | $CH_3OCH_3\ (g) \rightarrow 2(\text{---}CH_2\text{---})\ (g) + H_2O\ (g)$ | −110 kJ | Heat |
| 6. | $2CO_2\ (g) + 2H_2\ (g) \rightarrow +2O_2\ (g) + 2(\text{---}CH_2\text{---})\ (l)$ | −229 kJ | Heat balance |
| 7. | $4H_2O\ (g) \rightarrow 4H_2O\ (l)$ | −176 kJ | Heat of condensation |
| 8. | $2H_2O\ (l) + 2CO_2\ (g) \rightarrow +3O_2\ (g) + 2(\text{---}CH_2\text{---})\ (l)$ | 1305 kJ | Energy balance |

Formula 6 shows the balanced equation of all the reactions which occur after the electrolysis step, i.e., steps 2-5, and the total amount of generated heat is shown. Formula 7 shows the heat of condensation for the produced water that is recycled in the process. The overall chemical balance for steps 1-5 and the calculated overall energy consumption of the process is shown in Formula 8.

FIG. 1 describes the process and system for conversion which starts with the conversion of water to hydrogen via electrolysis. The water 2, led through pipe 112 is purified before electrolysis in a purification/filtration unit 8 and may therefore be of lower quality or where required, seawater may be utilized by using the appropriate purification methods. The purified water is electrolyzed in an electrolysis unit 4 to form hydrogen 6 and oxygen 7 in a 2:1 molar ratio. The oxygen 7 is pressurized (compressor 55 shown in FIG. 4 which illustrates further details of the electrolysis unit) and fed to storage tank 9, and will be partly utilized at a later stage in the process for recycling 7' of hydrocarbons not suitable for liquid fuels by partial oxidation or other processes described below. The hydrogen 6 is stored in an intermediate hydrogen storage tank 10 after compression (compressor 54 shown in FIG. 4) to assure that the process can be run continuously where electrical power availability varies, i.e., where electrical power is generated from solar or wind energy or where off-peak power is used.

The hydrogen 6 from the electrolysis unit 4 is transferred through line 116 and mixed with carbon dioxide 1 collected from industrial emission or other available sources, and passed through the unit 5 for purification and introduced through line 111 to produce a $H_2:CO_2$ mixture 11 of about 1:1 or any other mixture suitable for optimum performance of the RWGS reactor 13 in step two or alternatives thereof. The carbon dioxide may be captured from mixed industrial gas streams, used directly after purification 5 from concentrated carbon dioxide streams such as the emission from aluminum production or be from any other economically utilizable carbon dioxide source.

In step two, the $H_2:CO_2$ mixture 11 of 1:1 or any other suitable composition is fed to a compressor 16 through the line 12 and the compressed mixture is fed to reverse water gas shift (RWGS) reactor 13 converting the carbon dioxide and hydrogen mixture from tank 11 to carbon monoxide and water 14 according to Formula 2. Excess heat from other process steps is advantageously used to supply heat for this endothermic part of the process.

In step three the carbon monoxide is mixed with hydrogen in a molar ratio of $H_2:CO$ of 2:1, or any other ratio most suitable for methanol and/or dimethylether production. The gas mixture in mixing tank 17 may also contain $CO_2$ and $N_2$ or any other component that facilitates the conversion to methanol or makes the overall process more efficient. The gas mixture from tank 17 is fed through line 115 and compressor 18 to a methanol reactor 19 where the gas mixture is converted to methanol in a highly exothermic process, according to Formula 3.

In step four the crude methanol water mixture is fed through line 20 into a Methanol-to-Gasoline (MTG) reactor to be converted to high octane gasoline as described in the Mobil MTG process. The MTG reactor can be a fluidized-bed MTG reactor or a fixed-bed MTG reactor or any alternative thereof. If a two stage fixed-bed reactor is used, the first stage 21 where methanol is converted to DME may be decoupled from the second stage 26 (as shown in FIG. 1) and DME may be drawn as an end product from the production process.

Alternatively, the process may proceed directly with a $CO_2:H_2$ mixture of 1:3 or any other mixture suitable to produce methanol and/or dimethylether directly from $CO_2$ and $H_2$. The gas mixture in mixing tank 17 contains in this alternative primarily $CO_2$ and $H_2$ but may also contain CO and $N_2$ or any other component that facilitates the conversion to methanol or makes the overall process more efficient. The gas mixture from tank 17 is fed through line 115 and compressor 18 to a methanol reactor 19 where the gas mixture is converted to methanol 20 in an exothermic process, according to:

| | | | |
|---|---|---|---|
| 9. | $CO_2\ (g) + 3H_2\ (g) \rightarrow CH_3OH\ (g) + H_2O\ (g)$ | −47.7 kJ | Heat |

Figure 3:
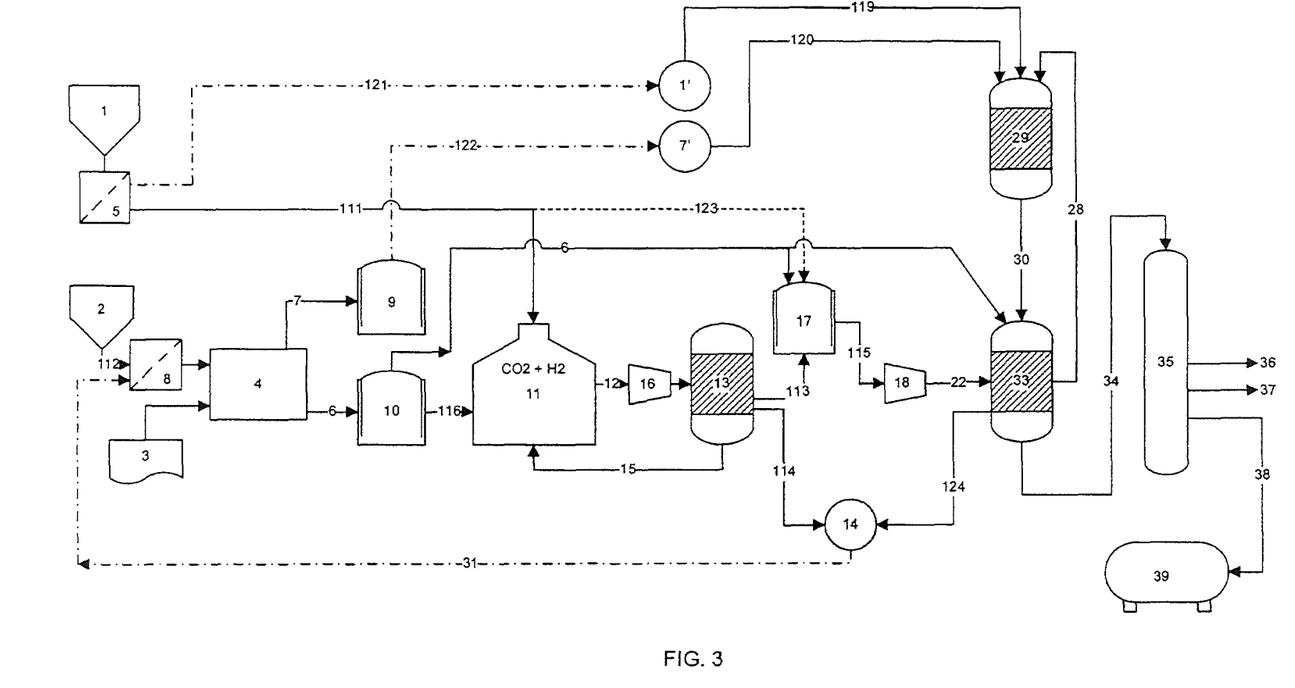
FIG. 3 shows an embodiment with a Fisher-Tropsch type reactor 33, which is fed with syngas and produces diesel.

In another alternative embodiment the process may proceed directly from step two to produce high cetane diesel or other hydrocarbon mixtures suitable to drive conventional combustion engines. In this case, as illustrated in FIG. 3, syngas 22 of suitable composition is fed directly to a Fisher-Tropsch ("FT") reactor 33 to preferably produce C10-C20 hydrocarbons. In a simplified reaction scheme the FT process can be described as follows:

$$(2n+1)H_2 + nCO \rightarrow +C_nH_{2n+2} + nH_2O \qquad 10.$$

The Fisher-Tropsch synthesis is a well developed process and a variety of reactor designs have been implemented. In this embodiment the syngas 22 is derived by mixing hydrogen from electrolysis of water with carbon monoxide from the RWGS reaction of carbon dioxide which gives easy and unlimited control over the syngas composition. This has two advantages with respect to the products from the FT reaction. Firstly, any desired syngas mixture may be produced as feed for the FT reactor, which allows much better control of the final product composition. Secondly, the $CO_2$ may easily be cleaned from sulfur containing compounds where necessary. The syngas so produced may therefore readily be obtained sulfur-free, leading to sulfur-free end product. Due to the flexibility in the composition of the syngas, the most preferred FT reactor type and synthesis conditions may be any that lead to the most desirable product mixture and the highest conversion efficiency. This will partly depend on market demands.

Figure 2:
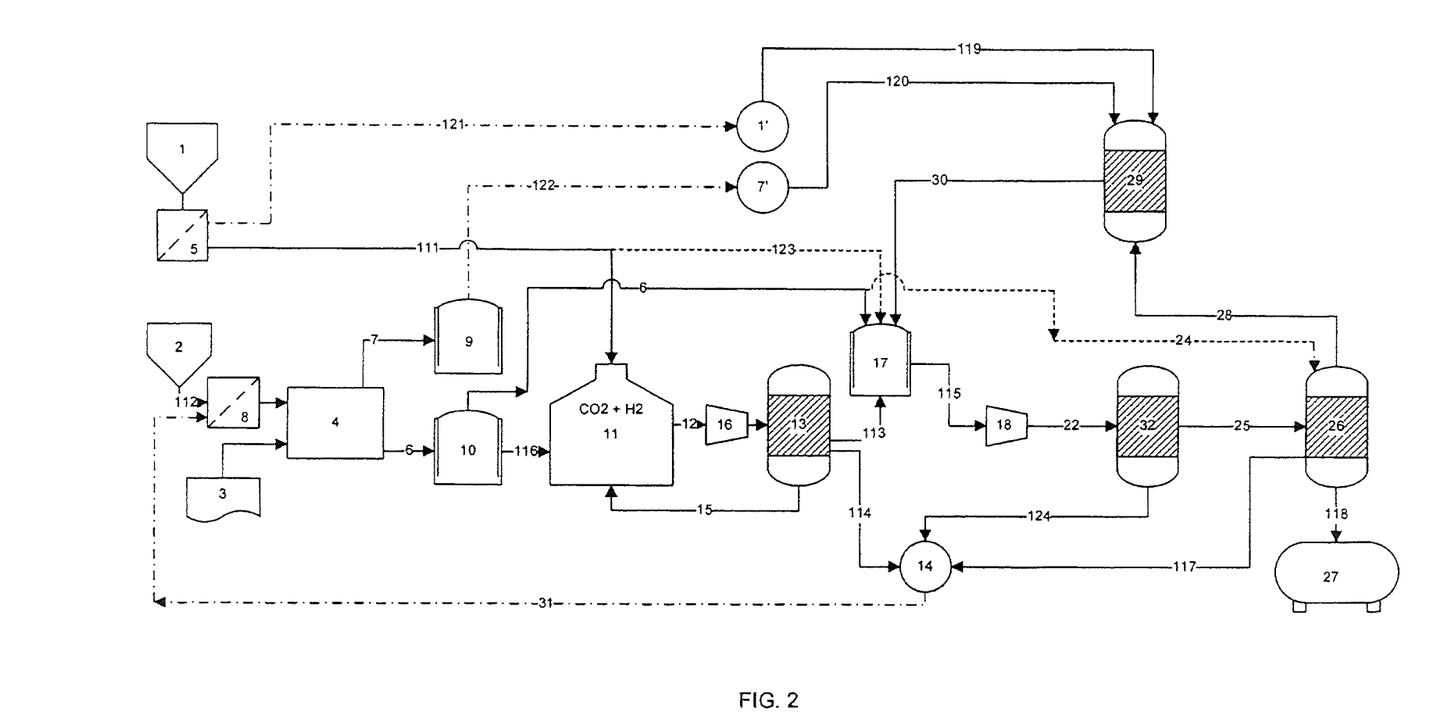
FIG. 2 shows an alternative embodiment similar to the system of FIG. 1, except, in this case syngas is fed to a combined methanol/DME reactor 32, coupled to the gasoline reactor.

Dimethyl ether 25 may also be produced directly from the syngas in step two without intermediate methanol production, as illustrated in FIG. 2. In that case a dehydration catalyst is mixed with the methanol synthesis catalyst in a slurry type reactor 32. This promotes the production of methanol and its conversion to DME in the same reactor. Thereby methanol is continuously withdrawn from the syngas to methanol equilibrium reaction promoting the syngas conversion. The same applies for the direct conversion of carbon dioxide and hydrogen to dimethyl ether. Dimethyl ether produced in this way may be utilized directly as fuel or for further conversion to gasoline or diesel.

Lower grade components 28 such as LPG (liquefied petroleum gas, which is a mixture of butane and propane, also referred to as autogas), fuel gas (C1 and C2 hydrocarbons) and other hydrocarbons not suitable for high octane fuel are preferably isolated and fed through line 28 (from the end product 27 which is directed through line 118 to storage tank 27) and are recycled. The recycling 29 is done by partial oxidation, steam reforming, autothermal reforming or by complete combustion. The products of the recycling step depend on the recycling method and reaction conditions. They may be hydrogen, carbon monoxide, carbon dioxide, water and heat. They will generally be fed appropriately back through line 30 into the production line.

Water 14 produced in steps two, three and four, or the above described alternatives thereof, may advantageously be collected by lines 114, 117 and 124 and fed back through return line 31 to the electrolyzer unit 4.

Heat produced in the exothermic reactions in steps three through five can be suitably used to drive the endothermic process in step two (the RWGS process). The remaining heat can be utilized for mechanical work such as compression.

In one preferred embodiment of the process invention compression work is minimized by operating the electrolysis for $H_2$ and $O_2$ production at high pressure and either utilizing liquid, compressed or frozen $CO_2$ or compressing $CO_2$ in multiple stages at as low a temperature as possible by cooling between stages with cold sea water or other heat sink.

FIG. 1 illustrates several of the above alternative embodiments. Carbon dioxide is fed from a source 1 through a purification unit 5 (desulphurization and/or other purification means, as needed, depending on the source and purity of carbon dioxide) through line 111 to mixing tank 11, generally after compression (not shown). A source of water 2 is fed through line 112 to a water purification unit 8, if needed, to an electrolysis unit 4, run by electrical power 3. The electrolysis unit is depicted in more detail in FIG. 4. The electrolysis unit 4 produces oxygen 7 and hydrogen 6, both of which would generally be compressed (compressors 54, 55 shown) and stored in intermediate storage tanks 9 and 10. The $CO_2$ and $H_2$ mixture may if needed be further compressed (in compressor 16) before being fed to the RWGS reactor 13. The products of which are shown as being separated in water 14 directed to line 114 and other products (CO and $H_2$ with residual $CO_2$) fed to syngas mixing tank 17. Further separation of the products from the RWGS step is illustrated in further detail in FIG. 5 described below. The syngas directed through line 115 is, if needed, compressed in compressor 18 before being fed to a methanol reactor 19 which produces methanol 20 fed to a DME reactor 21. Alternatively, $CO_2$ and $H_2$ may be fed directly to the methanol reactor 19 loaded with a suitable catalyst or catalyst mixture to convert $CO_2$ and $H_2$ directly to methanol. Independent of the production route, the produced methanol may be fed to a DME reactor 21 or directly through line 23 to the methanol-to-gasoline (MTG) reactor 26, which in such case is configured applicably.

In another embodiment, reactor 21 can be a combined MeOH/DME reactor being fed directly with syngas or a suitable mixture of hydrogen and carbon dioxide through line 22. The product from the final reactor is generally further separated and refined to provide the desired final product 27, which can be gasoline of any desired grade. Undesired hydrocarbons formed can be fed to oxidation unit 29 (various types as mentioned above), which is fed by oxygen 7', which advantageously is taken from the oxygen 7 produced by the electrolysis. The oxidation unit 29 is in some configurations further fed with $CO_2$ 1', and returns a product mixture 30, which is shown here as being delivered to the syngas mixing tank 17 (optional intermediate purification and storage not shown).

FIG. 2 shows an alternative embodiment, using a reactor 32 (e.g. slurry type reactor) comprising both dehydration catalyst and methanol synthesis catalyst, which reactor is fed directly with syngas through line 22. In this configuration dimethyl ether 25 is fed directly to the gasoline reactor 26.

FIG. 3 shows yet a further embodiment, with a Fisher-Tropsch type reactor 33 being fed with syngas 22 as discussed above.

DETAILED DESCRIPTION OF PREFERRED EMBODIMENTS

The overall process of the invention can be generally described as a process for producing liquid fuel and other hydrocarbon mixtures from carbon dioxide and water. The feedstock for the production is electricity, industrial carbon dioxide and water. The end product can be high octane gasoline, diesel or other liquid hydrocarbon mixtures suitable for driving conventional combustion engines. The end product can also comprise other hydrocarbons for further industrial processing or commercial use, and the end product may additionally or alternatively comprise dimethyl ether or methanol.

The overall process preferably comprises: electrolytic production of hydrogen from water; mixing of hydrogen to any desirable ratio with $CO_2$ to optimize the conversion of $CO_2$ to CO via the RWGS reaction, or to any ratio desirable to optimize methanol yield from a combined RWGS-reaction with methanol synthesis or to any ratio desirable to optimize direct methanol production from $CO_2$ and hydrogen; mixing of hydrogen to any desirable ratio with CO to produce syngas of optimal composition for any particular desired purpose, such as for the conversion of premixed synthesis gas to methanol, dimethyl ether or the direct conversion of the syngas to hydrocarbon products; synthesis of methanol directly from carbon dioxide and hydrogen or alternatively from the produced syngas; conversion of methanol to dimethyl ether (DME); conversion of DME to high octane gasoline; synthesis of high octane gasoline may also proceed directly from crude methanol; synthesis of high cetane diesel or other hydrocarbon mixtures may also proceed directly from the produced syngas; synthesis of dimethyl ether (DME) may also proceed directly from the produced syngas.

When hydrocarbon products such as high cetane diesel are produced, the premixed syngas (comprising the electrolytically produced hydrogen, $CO_2$ and the CO from the RWGS reaction of $CO_2$) is subjected directly to a Fisher-Tropsch synthesis. The syngas mixture can be optimized to maximize desired products yield.

Individual steps in the process are described in further detail below.

Step One: Electrolysis of Water to Produce Hydrogen

Figure 4:
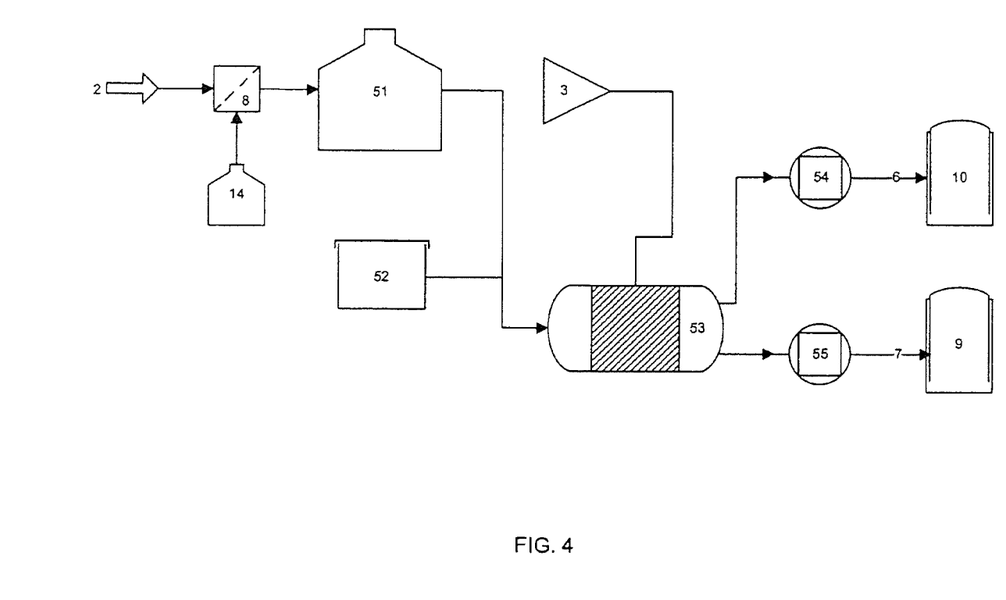
FIG. 4 illustrates a bipolar alkaline electrolyzer system which is useful for the system of the invention.

In the first step of the process, water 2 is electrolyzed in an electrolysis unit 4 to form hydrogen 6 and oxygen 7, which are formed in a 2:1 molar ratio. The oxygen is pressurized in compressor 55 and fed to storage tank 9 and will be partly utilized at a later stage in the process for recycling of hydrocarbons not suitable for liquid fuels by partial oxidation or other processes described herein. The excess oxygen is a valuable side product for industrial or commercial use. The hydrogen from the electrolyzer unit is typically compressed by compressor 54 and stored in an intermediate hydrogen storage tank 10 to assure that the process can be run continuously where electrical power availability varies, i.e., where electrical power is generated from solar or wind energy or where off-peak power is used.

The reaction is conveniently performed with state of the art Bipolar Alkaline Electrolyzer (BAE) units, or any other electrolyzer units equivalent or superior to the BAE units in production capacity and energy efficiency.

FIG. 4 shows a process flow diagram for hydrogen production based on the use of a BAE unit. The total efficiency of the electrolyzer unit is raised by about 10-15% by using excess energy from the recycling of hydrocarbons not suitable for use as liquid fuel, e.g. LPG, light fuel gas and higher hydrocarbons and/or by using excess energy from exothermic steps in the production process for compression of the gases and other energy demanding utilities. The figure shows a compressor 54 for compressing the generated hydrogen 6 and a compressor 55 for compressing the oxygen 7, both gases are conveniently stored in intermediate storage tanks, 9 (oxygen) and 10 (hydrogen). The water is obtained from any applicable source 2 and may optionally if needed be purified in a filtration unit 50. Water 14 produced from subsequent steps in the overall process may optionally be recycled for electrolysis. An electrolyte (KOH) source 52 is also shown as well as an electric power source 3. Some of the required electricity can be generated from the heat which forms in subsequent exothermic steps in the overall process. The electrolysis reactor 53 includes the electrolysis module itself, electrolyte circulation and hydrogen gas drying and purification means.

Step Two: Conversion of Carbon Dioxide to Carbon Monoxide

The hydrogen 6 obtained in step one is mixed with carbon dioxide 1 from industrial emission to produce a $H_2:CO_2$ mixture 11 preferably of a ratio of 1:1, however, any other mixture ratio may as well be used, which is suitable for optimum performance of a Reverse Water Gas Shift Reactor or alternatives thereof.

Conversion of carbon dioxide via the reverse Water Gas Shift Reaction (RWGSR):

$$CO_2(g)+H_2(g) \rightarrow CO(g)+H_2O(g). \Delta H=43.1 \text{ kJ/mol}$$

The mixture of $H_2$ and $CO_2$ is fed through a Reverse Water Gas Shift (RWGS) Reactor 13 charged with about 10 wt % Cu loaded g-alumina catalyst and/or other suitable catalysts to convert the carbon dioxide to carbon monoxide. The catalyst may be a commercially available CuO, ZnO and/or $Al_2O_3$ based catalyst but is not limited to those. The reactor is either run in recycling mode, with close to 100% equilibrium conversion, or alternatively conditions can be arranged to drive the reaction to complete consumption of one of the reactants by overload of the other and removal of products, preferably water. The water 14 from the exhaust is condensed and advantageously fed back through line 31 to the electrolyzes unit 4 and the carbon dioxide may be separated by isothermal compression and further cooling or by other suitable methods. The carbon dioxide is then fed back through 15 to the RWGS reactor 13. The remaining carbon monoxide and hydrogen may be fed directly to the syngas blender 17 or alternatively the hydrogen may be partly or fully separated from the gas mixture by membrane filtration and fed back to the RWGS reactor. Excess heat from other process steps is advantageously used to supply heat for this endothermic part of the process.

In an alternative embodiment, a suitable amount of $CO_2$ is provided to obtain a $H_2:CO_2$ reactant mixture of about 2:7 ratio, to which is mixed about 10% of a suitable buffer gas (e.g. Argon). Such mixture is fed through a Reverse Water Gas Shift Reactor loaded with about 5 wt % Cu/silica catalyst or other suitable catalysts to convert the carbon dioxide in to methanol and carbon monoxide, preferably with high methanol selectivity.

The methanol and the water formed in the reaction are separated from the exhaust by condensation and the carbon dioxide is separated from the remaining gases and fed back to the RWGS reagent gas blender. Carbon monoxide produced and remaining hydrogen is fed to the syngas blender.

With a suitable catalyst and by optimizing the reaction conditions i.e., the reactant ratio, the pressure and the space velocity, the product ratio of carbon monoxide to methanol can be optimized to an extent where the exothermic methanol synthesis supplies sufficient heat to run the mildly endothermic carbon monoxide production.

Figure 5:
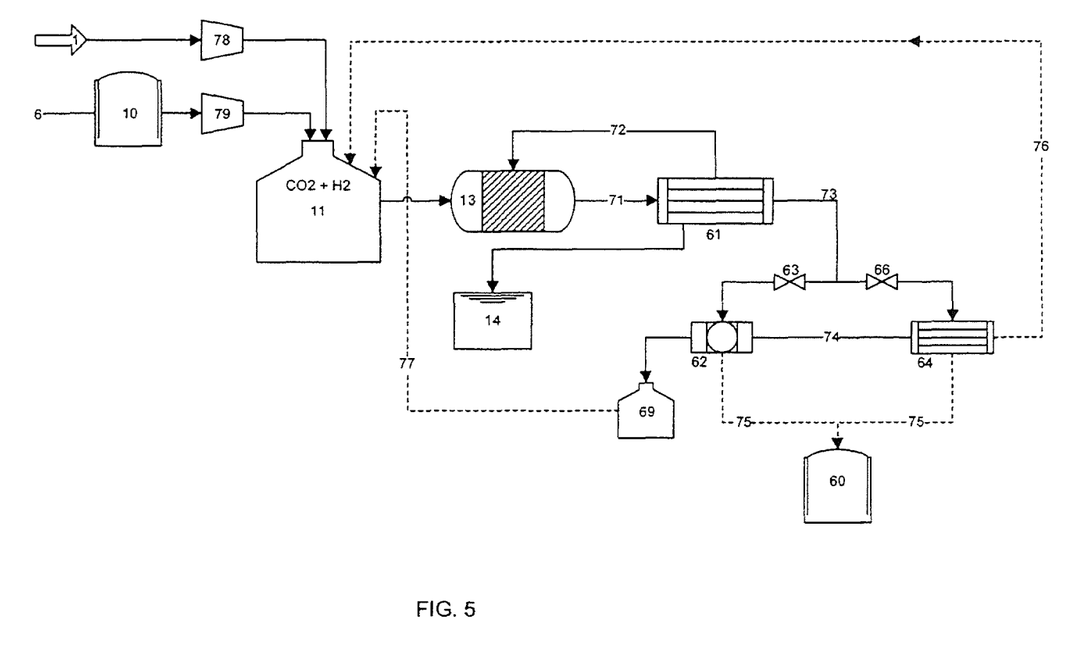
FIG. 5 shows in more detail one embodiment of a reverse water gas shift (RWSG) reactor system, which is part of the overall system of the present invention.

FIG. 5 illustrates a preferred embodiment of the RWGS step. $CO_2$ from an applicable source 1 is typically compressed by a compressor 78 before being fed to a $CO_2:H_2$ mixing unit, into which $H_2$ 6 formed in the electrolysis 4 is fed from an intermediate storage tank 10, optionally through a compressor 79, or the hydrogen may be stored under sufficient pressure. The $CO_2:H_2$ mix is fed to the RWGS reactor 13, the products of which are fed to a condenser, separating out produced water 14. The heat generated by condenser 61 is shown being supplied back to the reactor to drive the endothermic reaction. The products 73 are further fed to a membrane filtration unit 62 (in this case valve 63 is open and valve 66 is closed) to separate out hydrogen (to tank 69, from which the hydrogen can be recycled to the $CO_2:H_2$ blender), the thus obtained $CO:CO_2$ mixture is directed through line 74 to a condenser 64 for separating out $CO_2$ which can be fed through line 76 back to the mixing tank 11 and the CO is shown fed to tank 11. The arrangement shown with valves 63 and 66 is to illustrate that the order of the separation can be reversed (valve 66 open and 63 closed), first condensing out the $CO_2$ and subsequently removing $H_2$.

Step 3: Methanol Production from Hydrogen and Carbon Monoxide

In step three the carbon monoxide is mixed with hydrogen in a molar ratio of $H_2:CO$ of 2:1 and fed through a methanol reactor. The reactor is preferably a Liquid phase methanol reactor based on inert hydrocarbon media and conventional copper-zinc catalyst, such as described e.g. in U.S. Pat. No. 4,910,227. The methanol reactor may also be a multistage adiabatic reactor or a cooled tubular reactor as currently used in industrial methanol production. The methanol synthesis may also be carried out in the presence of a water-soluble basic substance where water is used as slurry medium, as disclosed in Japanese Patent No. 57126434 or with any other suitable slurry media or reactor type. The methanol thus formed can be pooled with methanol/water obtained in step 2, if methanol is being directly produced in step 2 as described above. The remaining gas reenters the reactor.

The methanol formation is a strongly exothermic process, which makes it difficult in practice to maintain constant and uniform temperature in isothermal reactors such as a tubular reactor. This may, however, be controlled to a large extent by controlling the composition of the syngas. As described above for step two, preferred embodiments allow complete control of the syngas composition. This is used to maximize the utilization of excess heat from this highly exothermic reaction and to maintain maximal control of the thermal conditions of the reactor. For example, the heat release may be increased by adding excess CO but may be reduced by adding a small amount of $CO_2$. Through better heat control byproducts such as higher alcohols, esters and ketones are minimized and the lifetime of the catalyst extended.

Alternative Embodiment:

Direct Methanol Production from Carbon Dioxide and Hydrogen

Carbon dioxide is reacted with hydrogen to produce methanol directly, that is, without a distinctly separate RWGS reaction step. Hydrogen reacts with carbon dioxide in a 3:1 ratio or any other desirable ratios to produce methanol and water in a 1:1 ratio. Hydrogen from electrolysis and carbon dioxide from emissions capture are here directly reacted over a $Cu/ZnO/Al_2O_3$, $Cu/ZrO_2$ or a CU—Zn—Cr based catalyst or any other catalyst suitable for the conversion of carbon dioxide and hydrogen to produce methanol and water.

A reactant circulation loop containing carbon dioxide and hydrogen carries a reactant mixture through a catalyst containing reactor, a counter-flow heat exchanger, a condenser, and a circulation pump. The reactant mixture prior to entering the reactor passes through the counterflow heat exchanger as the exiting reactant mixture passes through the counterflow heat exchanger in the opposing direction.

As the reactant mixture passes through the reactor, hydrogen and carbon dioxide react, forming methanol and water. The mixture approaches an equilibrium composition with 20 to 25% of the reactant mixture being converted to methanol and water. The methanol and water formed is condensed as it passes through the condenser. After passing through the circulation pump, additional carbon dioxide and hydrogen are added to replace that which has reacted to methanol and water.

The pressure in the loop is nominally about 50 bar and the temperature of the reactor is about 225° C. Methanol and water are condensed out of the loop by operating the condenser at 20° C.

Step Four: Methanol to Gasoline Process

In step four the crude methanol and water mixture from the direct conversion of carbon dioxide and hydrogen to methanol or methanol and water from the combined steps two and three is fed into a Methanol to Gasoline (MTG) reactor to be converted to high octane gasoline in the C5-C10 range. A suitable embodiment of this process, referred to as the Mobil MTG process, is described in detail in U.S. Pat. Nos. 4,788, 369, and 4,418,236. The process is originally described for a fixed-bed reactor but has also been developed for fluidized-bed reactors. The fixed-bed arrangement has been used in large industrial scale reactors used in the New Zealand GTG plants and the liquid-bed reactors have been demonstrated on commercial scale. The conversion of methanol to high octane fuel in this embodiment may be carried out in a fixed- or a fluidized bed Mobil MTG reactor but is not limited those particular reactor types. The advantage of the fluidized bed is the better heat control and the close to 100% conversion efficiency in one run. The advantage of the fixed-bed reactors is the extensive experience in their operation and that the methanol to gasoline synthesis runs in two steps where dimethyl ether may be withdrawn from the first step as final product.

Figure 6:
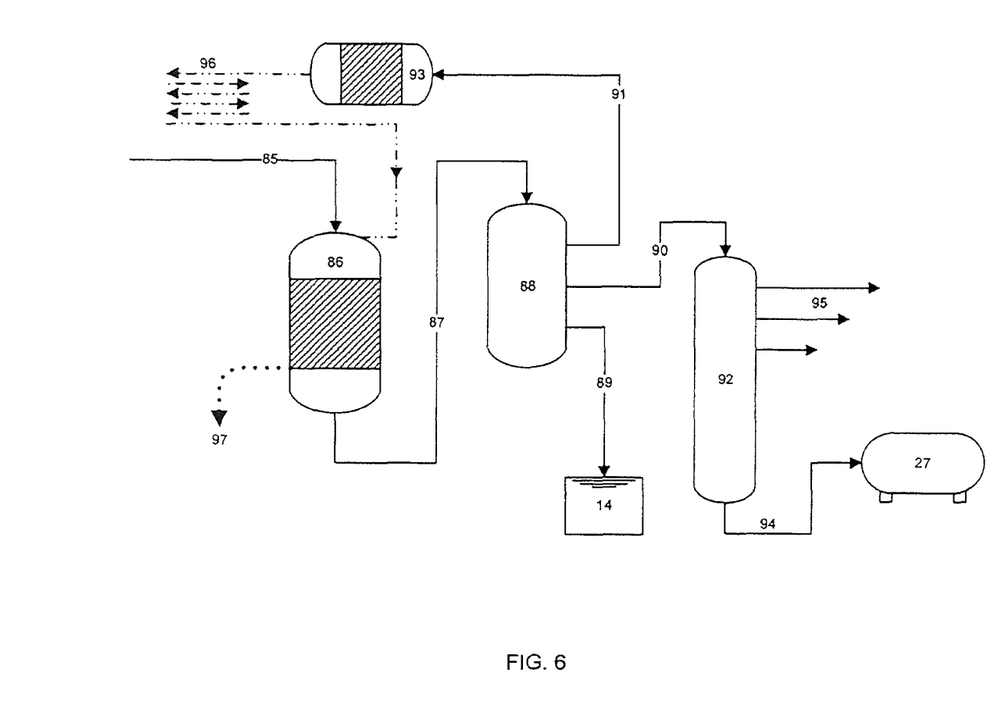
FIG. 6 shows a schematic overview of one type of methanol-to-gasoline (MTG) reactor system which forms part of the overall system of the invention.

FIG. 6 illustrates one embodiment of a useful setup for gasoline synthesis. Methanol (or alternatively dimethylether or a mixture thereof, depending on the configuration and catalyst composition of the reactor) is fed through in-feed line 85 to reactor 86 which delivers products to separator 88 and excess heat 97, which can advantageously be utilized elsewhere in the overall process as described herein. The separator separates out light weight hydrocarbons which are fed to a recycling oxidation unit 93, which can be set up to produce CO and/or CO", some of which may be fed back to reactor 86 or other precursor step in the overall process. Water is separated to storage 14, other hydrocarbon products are fed to further separation/refining to obtain the desired final gasoline product 27 and other hydrocarbon products 95 may be separated as well for further use and/or as a separate commodity.

Alternative to Step Three and Four: Syngas to Diesel or Other Hydrocarbon Mixtures Suitable to Drive Combustion Engines In an alternative embodiment, synthesis of high cetane diesel or other hydrocarbon mixtures may proceed directly from the syngas produced by electrolysis of water and the RWGS reaction of the produced hydrogen with carbon dioxide. In this embodiment a suitable $CO:H_2$ mixture, which may also be blended with other gas components such as $CO_2$ or buffer gas, is fed directly to a Fisher-Tropsch reactor. A suitable embodiment of this process is a reactor type which is based on the reactor design published in the article Fisher-Tropsch synthesis in Slurry Phase by M. D. Schliesinger et al. in Engineering and Process Development, vol. 43(6), 1474 (1951). A suitable adaptation of this reactor type is described in detail in U.S. Pat. No. 5,500,449. This adoption describes a slurry reactor which is loaded with a suitable catalyst and is typically operated around 250° C. and at 300 psia. However, due to the flexibility in the composition of the syngas, the most preferred FT reactor type and syntheses conditions may be any that lead to the most desirable product mixture and the highest conversion efficiency.

Figure 7:
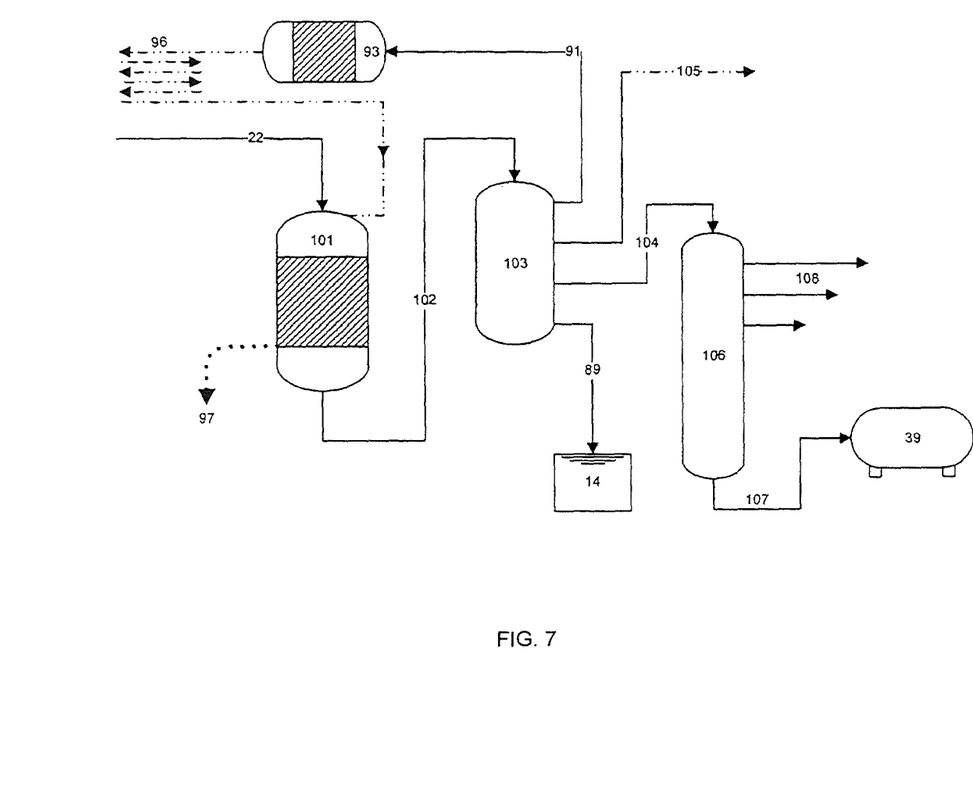
FIG. 7 illustrates a Fisher-Tropsch reactor used for the process described herein.

FIG. 7 shows a schematic setup of a Fisher-Tropsch type reactor arrangement, with an appropriate $CO:H_2$ mixture 22 being fed to reactor 101, the products of which are fed to separator 103 for further separation. The separator delivers water fed through 89 to storage 14, lighter hydrocarbons which are recycled to oxidation 93; CO from the oxidation recycling is fed back through 96 to reactor. Main hydrocarbon fraction 104 is fed to further refining/fractionation 106. High cetane diesel is fed through 107 to tank 39 and other products 108 which are as well of commercial value are separated and collected.

Recycling of Lower Grade Components Such as LPG, Fuel Gas and Other Hydrocarbons Not Suitable for Liquid Fuel In liquid fuel production from methanol or syngas, LPG and fuel gas may amount to 15%-40% of the product by weight depending on reactor type and reaction conditions. Those and other minor components are not suitable for liquid fuel or for further industrial processing or commercial use. To increase the efficiency of the overall process about 15-40%, all hydrocarbons not suitable for high octane fuel are recycled for further industrial processing or commercial use. The recycling may proceed through one of the following processes.

i) Through partial oxidation with pure oxygen from the electrolyzer unit in a partial oxidation reactor POX. The carbon monoxide hydrogen mixture formed is then blended with the premixed synthesis gas and fed to the liquid methanol reactor as described in step three. Carbon dioxide may also be blended to the POX reactor feed, resulting in additional CO output.

ii) Through steam reforming, whereby the hydrocarbon feed is blended with one to two carbon equivalent of $CO_2$ and about one to two hydrocarbon carbon equivalent of water steam. Depending on the CO to $CO_2$ ratio, the gas mixture resulting from the steam reforming process is fed directly to the syngas blender or RWGS reactant blender after condensation of the water steam, where advantageously, the gas mixture may be separated and fed back to the process as appropriate. Water is recycled in to the electrolyser unit.

iii) Through autothermal reforming, combining the partial oxidation process with steam reforming. This has the advantage that the heat from the exothermic partial oxidation helps drive the endothermic steam reforming process. Advantageously the pure oxygen for this process is delivered from the electrolyzer unit. After condensation of the water products, gas mixture may be fed directly to the syngas mixer, or the RWGS reactant blender depending on the $CO:CO_2$ ratio. The gas mixture formed may also be separated and fed back to the process as appropriate. Water is recycled in to the process.

iv) Through total oxidation, whereby the hydrocarbons not suitable for liquid fuel are burned with excess oxygen in a suitable heat exchanger to maximize exploitation of the heat released in this highly exothermic reaction. Advantageously the hydrocarbons are burned with pure oxygen from the electrolyzer unit. Water is separated from the carbon dioxide produced and fed back to the electrolyzer unit. The carbon dioxide formed is fed to the blender for the RWGS reactor. Heat released in the reaction is utilized in other process steps, such as compression, preheating of reactant streams, preferably the reactant stream for the RWGS reaction, or to drive endothermic reactions in this process.

Independent of the method used for recycling of lower grade components such as LPG or fuel gas, the heat recovered from the product gas mixture is used for compression, preheating of reactant streams, or to drive endothermic reactions in this process.

EXAMPLES

Herein below are described specific suitable arrangements and conditions for performing the process of the invention. These examples should not be considered as limiting the overall scope of the invention.

Example 1

Hydrogen Production Using a BAE-Unit of 2328 kW

Production capacity is 43.6 $kgH_2$/hr with a conversion efficiency of 80% (water to hydrogen) and an overall energy efficiency of 73% when the compression of hydrogen and oxygen is included.

The energy efficiency, which is calculated as the higher heating value (HHV) of hydrogen divided by the electrical energy consumed to produce one kg of hydrogen can advantageously be raised to about 83%.

This is done by utilizing excess energy from recycling of fuel gas, LPG and other hydrocarbons not suitable for liquid fuel and/or by using steam generated in the heat exchangers used to balance the highly exothermic methanol production, the MTG or the FT reaction for compression of the gases.

Example 2

Conversion of $H_2$ and $CO_2$ to Methanol in a Reaction Loop $H_2$ and $CO_2$ are supplied at 50 bar pressure and molar ratio of 3:1 ($H_2$ to $CO_2$) to a methanol synth reactor loaded with a $Cu/ZnO/Al_2O_3$, $Cu/ZrO_2$ or a CU—Zn—Cr based catalyst, or any other catalyst suitable for the conversion of carbon dioxide and hydrogen to produce methanol and water.

The reactor is operated at 225° C. and 20% of the input stream reacts to methanol and water in an equal molar ratio. After exiting the reactor, the output stream is cooled by counterflow heat exchange with the input stream. Then the output stream is further cooled so as to condense the reaction products (water and methanol). The condensed products are collected and periodically ejected, while the non-condensed gases are recirculated by a circulation pump and combined with new incoming input stream.

Example 3

Conversion of $CO_2$ to CO in an RWGS Reactor

The RWGS reaction is carried out in a fixed bed tubular reactor charged with 10 wt % Cu loaded g-alumina catalyst. The feed is a 1:1 mixture of $CO_2$ and $H_2$ at 400° C. and 5 bar. It has been shown that under those conditions higher than 95% equilibrium conversion may be achieved on a routine basis. At 400° C. the equilibrium constant for the reaction is about 0.08 which translates to about 27% $CO/CO_2$ ratio at 95% equilibrium conversion.

The conversion can be run in recycling mode, where exhaust water is condensed and fed back to the electrolyzer unit and the carbon dioxide may be separated by isothermal compression and further cooling or by other suitable methods. The carbon dioxide is then fed back to the RWGS reactor. The remaining carbon monoxide and hydrogen may be fed directly to the syngas blender or alternately the hydrogen may be partly or fully separated from the gas mixture by membrane filtration and fed back to the RWGS reactor. The excess heat removed from the exhaust gas and the heat of condensation from the water is fed back to the RWGS reactor through a counter flow heat exchanger.

The conversion may also be driven to complete consumption of $H_2$ by using an overload of $CO_2$ which is recycled and fed back to the reactor and/or by removing the water from the reactor by using desiccant beads or a condensing apparatus. Just the same, the reaction may be driven to complete $CO_2$ consumption by excess hydrogen and/or water removal. In that case the remaining exhaust water is removed by condensation and the excess hydrogen is separated from the exhaust through hydrogen permeable membrane filtration and feed back to the reactor.

Example 4

Conversion of $CO_2$ to CO at High Pressure to Produce Stoichiometric Syngas for Direct Feed to the Methanol Reactor With either excess $H_2$ or excess $CO_2$ it is possible to produce a syngas suitable for direct synthesis of crude methanol having the desired composition for subsequent conversion to gasoline or other liquid fuel.

In this example the RWGS reaction is carried out at 50 bar and 500° C. with a 10 wt % Cu loaded g-alumina catalyst. The catalyst may also be a commercially available CuO, ZnO and/or $Al_2O_3$ based catalyst but is not limited to those. In this example, where the produced syngas is intended as feed for a methanol reactor the preferred reactant ratio in the feed gas stream 2:1 ($H_2:CO_2$). A part of the $CO_2$ in the feed mixture is recycled from the reactor exhaust.

The high pressure chosen in this example has two main advantages.

Firstly, the high pressure is compatible with the requirement for removal of excess $CO_2$ by condensation. All utilizable heat may be withdrawn from the reactors exhaust as the water is condensed by cooling the exhaust to any suitable temperature lower than 265° C. $CO_2$ is condensed in a second step by cooling of the gas stream further, i.e., below 13° C. This may be done by transferring the waste heat to cold seawater or other suitable heat sink. Where a heat pump or refrigeration unit is necessary for this second step to reach the end temperature desired, the minimal temperature difference between hot and cold sides of the heat pump assures for optimal performance.

Secondly, after removal of water and $CO_2$ at 50 bar pressure, the RWGS reactor can feed directly into a methanol synthesis reactor of standard type, without additional compression. Compression can therefore be carried out on the $H_2$ and $CO_2$ feedstock at the lowest possible temperature to minimize energy required. At that point, prior to the RWGS reactor, $H_2$ and $CO_2$ feed streams can be cooled with available resources, such as cold seawater, for maximum compression efficiency. Multistage compression with intercooling between stages can approximate iso-thermal compression for maximum efficiency.

The higher temperature increases the equilibrium constant from about 0.08 at 400° to about 0.14 at 500° C. and thereby shifts the reaction equilibrium advantageously toward more CO formation.

Under those conditions the preferred reactant mixture of $H_2$ to $CO_2$ of 2:1 leads to the production of a stoichiometric syngas mixture that can be fed directly to the methanol reactor as described in step 3 above and example 4 below.

In this embodiment the $H_2:CO_2$ ratio may be tuned in any such way as to optimize the syngas mixture for its intended use, independent if it is intended as feed for a methanol reactor, dimethyl ether reactor, a Fisher-Tropsch reactor or any other reactor type advantageous for the disclosed process.

Example 5

Methanol Production in a Slurry Bubble Reactor

Methanol is produced in a slurry bubble reactor of LPMEOH™ type, such as are described in detail in Department of Energy/National Energy Technology Laboratory Report no. DOE/NETL-2004/1199 and U.S. Pat. No. 4,910,227. Typically, a syngas composition of about 60% CO, 25% $H_2$, 9% $CO_2$, and 4% $N_2$ enters the slurry reactor from the bottom. The feed stream is preheated to about 205° C. (400° F.) before entering the slurry bubble reactor which contains a slurry comprising in the range of 25-45 wt % BASF S3-85 catalyst or other suitable catalyst to convert syngas to methanol. The reactor is typically operated at about 725 psi and in the range of 200-290° C. (400-550° F.) at a gas hourly space velocity (GHSV) in the range of 5.000-10.000 standard liter/kg catalyst-hr. The methanol steam and remaining reactant gas disengages from the slurry and gathers in the slurry free zone at the top of the reactor from where it is collected. The exit gas is cooled in two steps. In the first step, vaporized oil from the slurry is condensed and brought back to the reactor, and in the second step the methanol/water vapor is condensed and the remaining syngas which still contains some mineral oil from the slurry and some minor amount of methanol is fed back to the feed stream. In this example the heat of the reaction is removed by steam generation in a cooling coil inundated in the slurry in the reactor. The superheated steam can be used for preheating chemical streams, compression of gases, driving of the endothermic RWGS reaction or for additional electricity production, Example 6

Conversion of Crude Methanol to Gasoline in a Fluidized-Bed Catalyst Process

The crude methanol which typically contains about 83% methanol and 17% water is injected as liquid or as superheated vapor at 413° C. in to a dense fluidized-bed catalyst reactor loaded with a ZSM-5 type catalyst or other suitable catalyst for the conversion of methanol to gasoline. A quantitative conversion is achieved in one pass at typical reaction conditions of 40-60 psia and 380-403° C. within the range of 500-1050 kg/hr methanol feed rate. The heat from the highly exothermic reaction is removed by steam generation in a cooling coil inundated in the slurry in the reactor. The superheated steam can be used for preheating chemical streams, compression of gases, driving of the endothermic RWGS reaction or for additional electricity production. After catalyst disengagement the product vapor is condensed, and the gasoline separated from the water. Fuel gas, LPG and other components not suitable for high octane gasoline are preferably separated from the gasoline fraction and fed to a partial oxidation reactor.

Example 7

Conversion of Crude Methanol to Gasoline in a Fixed-Bed Catalyst Process

In the fixed-bed MTG reactor the crude or dried methanol first enters a DME reactor where methanol undergoes a dehydration reaction in contact with an alumina catalyst at 300-420° C., to form an equilibrium mixture of methanol, water and dimethyl ether. The effluent from the DME reactor enters in a second stage a fixed-bed reactor loaded with Zeolite ZSM-5 catalyst where it is converted to gasoline products at 360-415° C. and 315 psig. The excess reagents from the second stage of this fixed bed MTG process are recycled by recombining them with the effluent from the first stage i.e. the DME reactor. The second stage is typically run with multiple reactors where one is always in regeneration mode.

The first stage in the fixed bed MTG process may be decoupled from the second stage to draw DME as an end product from the production process. In such case the reaction would be driven beyond equilibrium efficiency by removal of DME and water through evaporation of the DME and or condensation or desiccation to remove water.

Example 8

Production of Liquid Fuel Such as High Cetane Diesel Via Fischer-Tropsch Synthesis The Fisher-Tropsch (FT) synthesis is conducted in a slurry phase reactor where an iron catalyst is suspended in inert hydrocarbon media. The reactor is charged with inert hydrocarbon slurry with 5%-15% iron catalyst by weight with particle size ranging from 5 (micrometer) to 40 µm. The percentage of alkali metal and copper in the catalyst may be chosen to promote desired end products, but is preferably in the range of 0.005 to 0.015 and in the range of 0.005 to 0.050, respectively. Other catalysts that promote the FT synthesis in a desirable way may also be used. The operating pressure of the reactor is within the range from 100 psia to 500 psia and operating temperatures are in the range from 220° C. to 280° C. The preferred space velocity is between 100 and 300 cubic feet per hour per cubic feet of expanded catalyst bed. In this embodiment the most preferable reaction conditions for the FT synthesis are optimized to maximize the C10 to C20 fraction of the product for utilization as high cetane diesel. The heavier waxes are separated from the catalyst bed using a cross-flow filter and returning the catalyst to the reactor. The lighter hydrocarbons are separated by a cold trap or by distillation and fed directly to the hydrocarbon recycling unit which may be a POX reactor or another alternative as described above. The waxes can be converted to additional liquid fuel (Disel and Naphtha) by thermo cracking at 410° C. In this example the heat of the FT reaction is removed by steam generation in a cooling coil inundated in the slurry in the reactor. The superheated steam can be used for preheating chemical streams, compression of gases, driving of the endothermic RWGS reaction or for additional electricity production.

Example 9

Recycling of Hydrocarbons Not Suitable for High Octane Fuel by Catalytic Partial Oxidation and Use of Pure Oxygen from the Electrolyzer Unit a) Through Partial Oxidation of Fuel Gas and LPG The fuel gas and LPG fraction from the MTG or the FT synthesis may be recycled by non-catalytic or catalytic partial oxidation.

In non-catalytic partial oxidation a burner is fed a mixture of oxygen and hydrocarbons containing about 0.45 carbon equivalent of pure oxygen from the electrolyses process described in step one and example 1.

The gas mixture is brought to ignition temperature by an external source and the gas feed is adjusted to optimize performance. As the ignition may require higher oxygen content than optimal for the POX reaction and therefore different burner design, the ignition may be assisted by a catalyst.

The partial oxidation may also be carried out using a catalyst as described in a number of patent documents, e.g., U.S. Pat. Nos. 4,844,837; 4,087,259, 5,648,582 and 6,254,807. In one example of the catalytic POX reaction an oxygen/hydrocarbon mixture containing 0.4-0.6 carbon equivalent of oxygen is preheated to about 200° C. The oxygen/hydrocarbon mixture is fed to a POX reactor with a monolith catalyst that has been preheated with an external source to a temperature close to the ignition temperature. After ignition a monolith catalyst temperature of near 1000° C. is established and no further external energy is required.

Independent of the POX reactor type, carbon dioxide may be mixed to the oxygen/hydrocarbon feed to reduce formation of elemental carbon and to increase the CO production.

The product gas is cooled in a suitable heat exchanger to utilize the excess heat for compression or other energy demanding steps in the process. If the syngas is intended for synthesis, such as the methanol synthesis, where the syngas is preheated, it is preferable to retain the appropriate portion of the excess heat in the product, wherein the hot product gas enters preferably directly the syngas blender, where it is balanced.

b) Through Steam Reforming of Fuel Gas and LPG.

In this example steam reforming is conducted substantially as described in U.S. Pat. No. 5,500,449. The gas stream containing the lighter hydrocarbons is mixed with one to two carbon equivalent of carbon dioxide to prevent elemental carbon production. The carbon dioxide and hydrocarbon gas mixture is then mixed with steam to produce a mixture containing about 1 mol carbon from hydrocarbons to 1-2 mole water. Preferably the steam needed for the steam reforming is branched of the superheated water steam from the heat exchanger in the methanol-, MTG- or FT-reactor. The preheated gas/steam mixture enters a conventional steam reforming reactor charged with commercially available Nicel catalyst. The conversion of the hydrocarbons to carbon monoxide and hydrogen takes place at 700° C.-900° C. at a system pressure that may be between 12 and 500 psia. A typical flow rate for such reactor would be about 300 lbs/hr/cubic feet of catalyst. After condensation of the water the product gas from the steam reforming may be fed directly to the syngas mixer or may be freed from carbon dioxide and other minor components first, depending on the intended application of the syngas.

The invention claimed is:

1. A system for production of liquid fuel from carbon dioxide and water using electricity, the system comprising:
    (a) a purification unit in fluid communication with stack gas units of industrial plants and/or power plants, said purification unit arranged and designed to separate the carbon dioxide from stack gases;
    (b) an electrolysis unit arranged to convert water into hydrogen and oxygen;
    (c) a first mixing unit disposed downstream of and in fluid communication with said purification unit and said electrolysis unit to mix said carbon dioxide and said hydrogen;
    (d) a catalytic reactor disposed downstream of and in fluid communication with the said first mixing unit to receive the mixture of said carbon dioxide and said hydrogen and to produce methanol and carbon monoxide and said water;
    (e) a second mixing unit disposed downstream of and in fluid communication with the said catalytic reactor, said second mixing unit arranged and designed to accept a portion of said carbon monoxide;
    (f) a liquid fuel generation unit disposed downstream of and in fluid communication with said second mixing unit, said liquid fuel generation unit arranged and designed to receive and convert a portion of said carbon monoxide in the presence of a substantially pure hydrogen gas to produce said liquid fuel; and
    (g) an oxidation unit disposed downstream of and in fluid communication with said liquid fuel generation unit, said oxidation unit arranged and designed to oxidize any unaccepted portion of separated hydrocarbon product under conditions producing a combustion product comprising said hydrogen, said carbon monoxide, said carbon dioxide and said water.

2. The system of claim 1, wherein said catalytic reactor further comprises a reverse water gas shift reactor for the formation of said carbon monoxide.

3. The system of claim 1, wherein said second mixing unit is disposed downstream of said purification unit to receive a direct supply of said carbon dioxide.

4. The system of claim 1, wherein said second mixing unit directly supplies a mixture of said carbon dioxide and said hydrogen to said liquid fuel generation unit for the production of said liquid fuel.

5. The system of claim 1, wherein said liquid fuel generation unit further comprises of series of reactors used for the production of said liquid fuel.

6. The system of claim 1, wherein said liquid fuel generation unit comprises at least one of a methanol reactor, a methanol-to-gasoline reactor, and a Fischer-Tropsch reactor.

7. The system of claim 1, wherein said second mixing unit further comprises at least one control valve to feed various amounts of mixture of said carbon monoxide and said hydrogen to said liquid fuel generation unit to produce desired proportions of said liquid fuel.

8. The system of claim 1, wherein said second mixing unit is disposed downstream of and in fluid communication with said electrolysis unit to receive said hydrogen gas.

9. The system of claim 1, wherein said oxidation unit is in fluid communication with said second mixing unit to provide said carbon dioxide.

10. The system of claim 1, wherein said oxidation unit is at least one of a complete oxidation chamber, a partial oxidation chamber, a steam reformer and an auto reformer.

* * * * *